US00PP11216P

United States Patent [19]

Moerenhout

[11] Patent Number: Plant 11,216

[45] Date of Patent: Feb. 8, 2000

[54] HYBRID TEA ROSE PLANT NAMED 'MOERIGNA'

[76] Inventor: Eric Moerenhout, Proefhovestraat 3, 9090 Gontrode/Melle, Belgium

[21] Appl. No.: 09/005,579

[22] Filed: Jan. 12, 1998

[51] Int. Cl.[7] ..... A01H 5/00

[52] U.S. Cl. ..... Plt./130

[58] Field of Search ..... Plt./130, 131, 135, Plt./136, 141, 142, 146, 147

[56] References Cited

U.S. PATENT DOCUMENTS

P.P. 3,229 7/1972 Kordes ..... Plt./142
P.P. 9,052 2/1995 Heursel ..... Plt./131
P.P. 9,997 8/1997 Meilland ..... Plt./130

*Primary Examiner*—Howard J. Locker
*Attorney, Agent, or Firm*—Burns, Doane, Swecker & Mathis, L.L.P.

[57] ABSTRACT

A new and distinct variety of Hybrid Tea rose plant is provided that abundantly forms attractive double flowers that are bicolored orange veined with yellow in coloration. The buds are very long and are slow opening. Such flowers exhibit a good vase life and possess petals that detach cleanly. The plant exhibits a narrow bushy growth habit, forms semi-vigorous vegetation, and is particularly well suited for greenhouse forcing for cut flower production. Additionally, the plant is resistant to diseases when grown under greenhouse conditions.

1 Drawing Sheet

SUMMARY OF THE INVENTION

The new variety of Hybrid Tea rose plant was created by artificial pollination wherein two parents were crossed which previously had been studied in the hope that they would contribute the desired characteristics. The female parent (i.e., the seed parent) was the 'Matador' variety (U.S. Plant Pat. No. 3,229). The 'Matador' variety sometimes is known as the 'Ester O'Farim' variety and the 'Korfarim' variety. The male parent (i.e., the pollen parent) was a seedling of the 'Korenlo' variety (U.S. Plant Pat. No. 5,679). The 'Korenlo' variety is marketed under the LORENA trademark. The parentage of the new variety can be summarized as follows:

'Matador'×Seedling of 'Korenlo'.

The seeds resulting from the above pollination were sown and 382 small plantlets were obtained which were physically and biologically different from each other. Selective study resulted in the identification of a single plant of the new variety.

It was found through careful study that the new variety of the present invention exhibits the following combination of characteristics:

(a) from a physical point of view forms green mature wood, assumes a narrow bushy growth habit, and forms attractive long-lasting bicolored orange veined with yellow double flowers having consistent petals, and
(b) from the biological point of view forms semi-vigorous vegetation, produces flowers in abundance, exhibits the ability readily to be forced, and is resistant to diseases when grown under greenhouse conditions.

The new variety well meets the needs of the horticultural industry and is particularly well suited for growing in the greenhouse for the production of attractive long-lasting cut flowers that are orange veined with yellow.

The new variety can be readily distinguished from other varieties including the parent varieties in view of the combination of characteristics described herein. For instance, the parent 'Matador' variety forms scarlet and orange blossoms that are golden yellow on the reverse, and 'Korenlo' variety forms salmon pink blossoms. It exhibits straight stems, rigid and straight peduncles, a good ability to be forced under greenhouse conditions, and a long vase life for its distinctive bicolored orange veined with yellow flowers. The flowers exhibit a negligible propensity to fade as they mature.

The new variety has been found to undergo asexual propagation and can be readily reproduced by conventional routes, such as budding (i.e., eye grafting). This asexual reproduction by budding as performed at Hyéres, France, has demonstrated that the characteristics of the new variety are strictly transmissible from one generation to another and are firmly fixed.

The new variety has been named the 'Moerigna' variety.

BRIEF DESCRIPTION OF THE PHOTOGRAPH

The accompanying photograph shows as nearly true as it is reasonably possible to make the same in a color illustration of this character typical specimens of the plant parts of the new variety. The rose plants of the new variety were grown under glass in the South of France.

DETAILED DESCRIPTION

Figures 1, 2, 3, 4, 5, 6, 7, 8, 9, 10, 11, 12, 13, 14, 15, 16, 17, 18, 19:
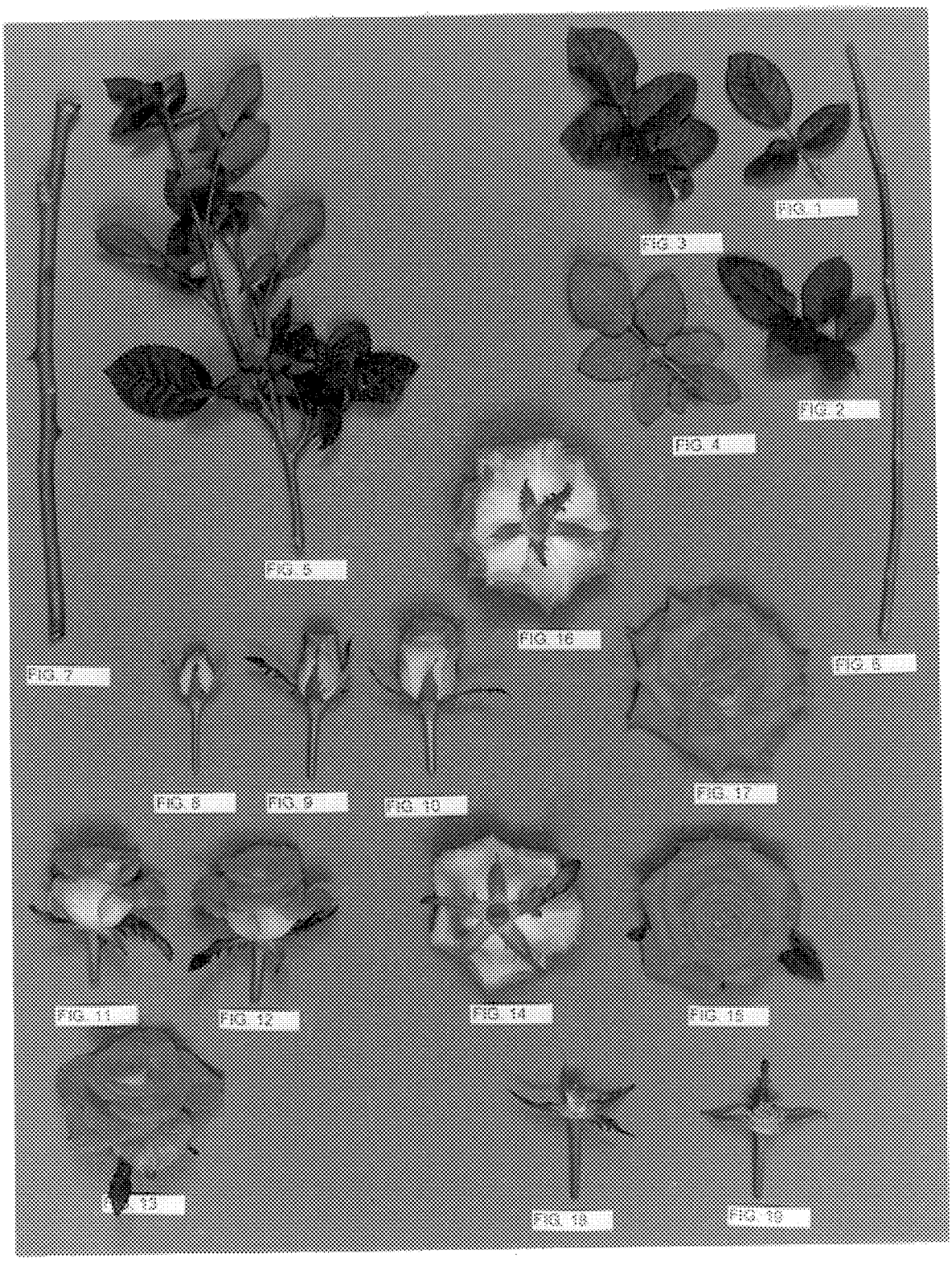
FIG. 1 illustrates a specimen of a leaf with three leaflets—plan view—upper surface.
FIG. 2 illustrates a specimen of a leaf with five leaflets—plan view—upper surface.
FIG. 3 illustrates a specimen of a leaf with seven leaflets—plan view—upper surface.
FIG. 4 illustrates a specimen of a leaf with seven leaflets—plan view—under surface.
FIG. 5 illustrates a specimen of a young shoot.
FIG. 6 illustrates a specimen of a flowering stem.
FIG. 7 illustrates a specimen of a main branch.
FIG. 8 illustrates a specimen of a floral bud at the opening of the sepals.
FIG. 9 illustrates a specimen of a floral bud in a more advanced stage of opening than as illustrated in FIG. 8.
FIG. 10 illustrates a specimen of a floral bud at the opening of the petals.
FIG. 11 illustrates a specimen of a flower at an early stage in the course of opening.
FIG. 12 illustrates a specimen of a flower in a more advanced stage of opening than as illustrated in FIG. 11.
FIG. 13 illustrates a specimen of a flower in a more advanced stage of opening than as illustrated in FIG. 12.
FIG. 14 illustrates a specimen of an open flower—plan view—reverse.
FIG. 15 illustrates a specimen of an open flower—plan view—obverse.
FIG. 16 illustrates a specimen of a fully open flower—plan view—reverse.
FIG. 17 illustrates a specimen of a fully open flower—plan view—obverse.
FIG. 18 illustrates a specimen of a floral receptacle showing the arrangement of the pistils (a sepal and stamens are removed)
FIG. 19 illustrates a specimen of a floral receptacle showing the arrangement of the stamens and pistils (two sepals are removed).

The chart used in the identification of the colors is that of The Royal Horticultural Society (R.H.S. Colour Chart). The description is based on the observation of plants grown under glass in the South of France. The coloration in common terms sometimes also is provided.

Class: Hybrid Tea.

Plant:

*Height.*—Plants which were pruned to a height of 80 cm. produce floral stems having a length of approximately 30 to 60 cm., and an average length of approximately 40 cm.

*Habit.*—Narrow bushy. Under greenhouse growing conditions with the use of conventional pruning the plant commonly assumes a height of approximately 1.8 m. and a width of approximately 0.8 m.

Branches:

*Color.*—Young shoots: when approximately 20 cm. long, exhibit a green coloration, Yellow-Green Group 146B with bronze. Floral stems: Yellow-Green Group 144A to 146C. Mature wood: Yellow-Green Group 146B.

*Thorns.*—Configuration: concave on the upper and under edges. Quantity: young shoots commonly are thornless, and on a typical stem having a length of 10 cm. sometimes 1 to 5 long prickles and a few short prickles commonly are present depending on the season and the cultural conditions. Length: approximately 6 mm. on average on floral stems and approximately 6.5 mm. on average on mature wood, and commonly range from approximately 4 to 7 mm. in each instance. Color: on floral stems the coloration of the thorns is reddish, and on mature wood the coloration of the thorns is Grey-Brown Group 199A and 200D.

*Leaves.*—Number: typical for the class. Size: medium. Stipules: adnate and medium.

*Leaflets.*—Number: rarely 1, and commonly 3, 5 and 7. Size: medium. Shape: rounded at the base, cordate at the intersection with the petiole, slightly concave in the cross-section; and possess weak to medium margin undulation. Serration: present, single, regular, and not strongly marked. General appearance: thin, weak. Petiole: the inner surface is grooved with non-glandular edges. Petiole color on young shoot: Greyed-Purple Group 183B on inner and outer surfaces. Petiole color on floral stem: Yellow-Green Group 146C to 146D at the middle and Yellow-Green Group 146A at the edges of the inner surface, and Yellow-Green Group 146B to 146C on the outer surface. Petiole color on mature wood: Yellow-Green Group 146D on inner surface, and Yellow-Green Group 146C on outer surface. Petiole length of terminal leaflet: approximately 12 to 17 mm., approximately 14 mm. on average, with a standard deviation of 2 mm. on a leaf of 5 leaflets. Terminal leaflet length: approximately 42 to 64 mm., approximately 55 mm. on average, with a standard deviation of 5 mm. on a leaf of 5 leaflets. Terminal leaflet width: approximately 32 to 42 mm., approximately 38 mm. on average, with a standard deviation of 4 mm. on a leaf of 5 leaflets. Terminal leaflet shape at base: rounded and slightly cordate at the intersection with the petiole. Leaflet color of young shoot: Green Group 137A with some reddish coloration on the upper surface, and Greyed-Purple Group 183B to 183C on the under surface. Leaflet color on floral stem: Yellow-Green Group 147A on the upper surface and Yellow-Green Group 147B to 147C on the under surface. Leaflet color of mature wood: Yellow-Green Group 147B on the upper surface, and Yellow-Green Group 147C on the under surface.

Inflorescene:

*Number of flowers.*—Generally one to four per stem when grown under forced greenhouse conditions.

*Peduncle.*—Erect, stiff, Yellow-Green Group 146C, commonly without hairs, and commonly approximately 9 to 13 cm. in length (approximately 11 cm. in length on average).

*Sepals.*—Configuration: Two sepals commonly possess no extensions, and three sepals commonly possess extensions (as illustrated). The sepal length commonly ranges from approximately 3 to 4 cm. on average. Color: Yellow-Green Group 146D on the upper surface and Yellow-Green Group 146C on the under surface.

*Buds.*—Shape: ovate. Size before calyx breaks: the bud lengths commonly are approximately 33 to 44 mm., with an average length of approximately 37 mm. Color as calyx breaks: Orange-Red Group 30A on the inner surface, and Yellow Group 12C to 12D edged with Orange-Red Group 30A on the outer surface. Size after calyx breaks: the bud lengths commonly are approximately 38 to 45 mm., with an average length of approximately 40 mm.

*Flower.*—Time: medium flowering. Shape: double. Form: star-shaped when viewed from above, flattened convex to convex at the upper part when viewed from the side, and flattened convex at the lower part when viewed from the side. Diameter: medium to large, commonly approximately 80 to 93 mm., and approximately 90 mm. on average, with a standard deviation of 2 mm. Petal number: commonly approximately 30 to 35, with an average of approximately 32, commonly plus approximately 10 to 15 small petals. Petal size (second row from outside): the length is approximately 38 to 42 mm. with a mean of approximately 40 mm., and a standard deviation of 2 mm., and the width is approximately 40 to 53 mm. with a mean of approximately 45 mm., and a standard deviation of 3 mm. Petal shape: flattened convex with medium to strong reflexing of the margin and weak to very weak undulation of the margin. Petal color: The following description of a nearly fully open flower was made while observing a rose grown in the greenhouse during September which had been undergoing opening for 3 days. Petal color (middle zone): on the inner surface. Orange-Red Group 30A and on the outer surface creamy yellow, Yellow Group 12D, with some orange coloration and finishing to near Yellow Group 11D to Yellow-White Group 158D at the end of complete opening. Petal color (marginal zone): on the inner surface. Orange-Red Group 30A and the outer surface Orange-Red Group to Orange-Red Group 32A. Petal spot at base: Color of spot inner side: Yellow Group 9A finishing to Yellow Group 9C at the end of complete opening. Color of spot outer side: Yellow Group 9B and disappearing substantially completely at the end of full opening. Size: medium. Stamens: approximately 50 in number and are somewhat regularly arranged around the pistil. Filaments: medium in length and Yellow Group 13B in coloration. Anthers: medium in size, all open at approximately the same time, and the immature coloration is Yellow Group 13B. Pollen: sparse in quantity and Yellow Group 4D in coloration. Pistils: approximately 80 in number. Styles: medium in length and Yellow Group 9D at the base and Red Group 46B at the top. Stigmas: Yellow Group 9D, and generally extend slightly above the anthers. Hips: no hips have been observed to date. Seeds: none observed to date. Petal drop: petals detach cleanly. Fragrance: none. Lasting quality: very good. When cut and placed in a vase, the flowers commonly last approximately 8 to 10 days. When left on plant, the flowers commonly last approximately 12 to 15 days.

*Productivity.*—good with approximately 160 flowers per square meter being formed per year.

Development:

*Vegetation.*—Semi-vigorous.

*Blooming.*—Abundant and almost continuous.

*Aptitude to forcing.*—Very good.

*Resistance to diseases.*—Good under greenhouse conditions, and sensitive to powdery mildew when grown outdoors.

I claim:

1. A new and distinct variety of Hybrid Tea rose plant characterized by the following combination of characteristics:

(a) from a physical point of view forms green mature wood, assumes a narrow bushy growth habit, and forms attractive long-lasting bicolored orange veined with yellow double flowers having consistent petals, and (b) from the biological point of view forms semi-vigorous vegetation, produces flowers in abundance, exhibits the ability readily to be forced, and is very resistant to diseases when grown under greenhouse conditions;

substantially as herein shown and described.

* * * * *